US010881483B2

United States Patent
Nahum et al.

(10) Patent No.: US 10,881,483 B2
(45) Date of Patent: Jan. 5, 2021

(54) NEUROSURGICAL ASSISTANCE ROBOT (71) Applicant: MedTech S.A., Montpellier (FR)

(72) Inventors: Bertin Nahum, Baillargues (FR);
Fernand Badano, Villeurbanne (FR);
Eric Roussel, Mas de Londres (FR);
Lucien Blondel, Montpellier (FR)

(73) Assignee: MedTech S.A., Montpellier (FR)

( * ) Notice: Subject to any disclaimer, the term of this patent is extended or adjusted under 35 U.S.C. 154(b) by 496 days.

(21) Appl. No.: 15/576,170

(22) PCT Filed: May 19, 2016

(86) PCT No.: PCT/FR2016/051178
§ 371 (c)(1),
(2) Date: Nov. 21, 2017

(87) PCT Pub. No.: WO2016/185140
PCT Pub. Date: Nov. 24, 2016

(65) Prior Publication Data
US 2018/0132965 A1 May 17, 2018

(30) Foreign Application Priority Data
May 21, 2015 (FR) ..................................... 15 01055

(51) Int. Cl.
*A61B 90/50* (2016.01)
*A61B 34/30* (2016.01)
(Continued)

(52) U.S. Cl.
CPC .............. *A61B 90/50* (2016.02); *A61B 34/30* (2016.02); *A61B 90/14* (2016.02); *A61G 13/121* (2013.01)

(58) Field of Classification Search
CPC ......... A61B 90/50; A61B 34/30; A61B 90/14; A61G 13/121
See application file for complete search history.

(56) References Cited

U.S. PATENT DOCUMENTS 4,979,949 A * 12/1990 Matsen, III ............ A61B 17/15
606/53
5,086,401 A * 2/1992 Glassman .............. B25J 9/1679
700/259
(Continued)

FOREIGN PATENT DOCUMENTS

| CA | 2896381 A1 * | 9/2014 | ......... A61B 17/3421 |
| CN | 101090678 A | 12/2007 | |

(Continued)

OTHER PUBLICATIONS

"European Application Serial No. 16733137.0, Response filed Aug. 8, 2018 to Office Action dated Jan. 31, 2018", 15 pgs.
(Continued)

*Primary Examiner* — Julian W Woo
(74) *Attorney, Agent, or Firm* — Schwegman Lundberg & Woessner, P.A.

(57) ABSTRACT

The disclosed subject matter relates to a neurosurgical assistance robot including a movable box the chassis of which is provided with a rigid support arm for connection to a headrest supporting the head of a patient lying on an operating table. Accore invention disclosed subject matter, the support arm is movable with respect to the chassis between a position retracted in the volume of the box and a plurality of extended positions, and a mechanism for locking the arm in any iled being provided for.

21 Claims, 5 Drawing Sheets

(51) Int. Cl.
*A61B 90/14* (2016.01)
*A61G 13/12* (2006.01)

(56) References Cited

U.S. PATENT DOCUMENTS

| | | | | |
|---|---|---|---|---|
| 5,147,287 A * | 9/1992 | Jewell | ............ | A61G 13/12 |
| | | | | 5/622 |
| 5,997,176 A * | 12/1999 | Fairleigh | ............ | A61B 6/501 |
| | | | | 378/195 |
| 6,033,415 A * | 3/2000 | Mittelstadt | ............ | G06T 3/0006 |
| | | | | 128/922 |
| 6,441,577 B2 * | 8/2002 | Blumenkranz | ............ | B25J 9/1689 |
| | | | | 128/DIG. 7 |
| 6,723,106 B1 * | 4/2004 | Charles | ............ | B25J 9/1065 |
| | | | | 606/130 |
| 7,306,612 B1 * | 12/2007 | Landa | ............ | A61B 90/17 |
| | | | | 5/622 |
| 8,005,571 B2 * | 8/2011 | Sutherland | ............ | A61B 90/25 |
| | | | | 700/248 |
| 2006/0288484 A1 * | 12/2006 | Roleder | ............ | A61H 37/00 |
| | | | | 5/622 |
| 2010/0137880 A1 | 6/2010 | Nahum et al. | | |
| 2011/0162476 A1 * | 7/2011 | Nakamura | ............ | A61B 90/50 |
| | | | | 74/490.01 |
| 2014/0314538 A1 * | 10/2014 | Carter | ............ | A61B 90/50 |
| | | | | 414/744.3 |

FOREIGN PATENT DOCUMENTS

| | | |
|---|---|---|
| CN | 203042855 U | 7/2013 |
| CN | 103533894 A | 1/2014 |
| CN | 204106426 U | 1/2015 |
| CN | 108076623 | 5/2018 |
| JP | 2010530268 A | 9/2010 |
| JP | 2014511186 A | 5/2014 |
| JP | 2018516728 | 6/2018 |
| WO | WO-2009013406 A2 | 1/2009 |
| WO | WO-2013192598 A1 | 12/2013 |
| WO | WO-2016185140 A1 | 11/2016 |

OTHER PUBLICATIONS

"International Application Serial No. PCT/FR2016/051178, International Search Report dated Jul. 27, 2016", With English Translation, 5 pgs.

"International Application Serial No. PCT/FR2016/051178, Written Opinion dated Jul. 27, 2016", With English Translation, 11 pgs.

"Australian Application Serial No. 2016263539, First Examination Report dated Apr. 24, 2020", 3 pgs.

"Australian Application Serial No. 2016263539, Subsequent Examiners Report dated Jul. 20, 2020", 3 pgs.

"Chinese Application Serial No. 201680034005.3, Office Action dated Apr. 27, 2020", (W/ English Translation), 14 pgs.

"Japanese Application Serial No. 2018-512498, Office Action dated Mar. 24, 2020", (W/ English Translation), 5 pgs.

"Japanese Application Serial No. 2018-512498, Response filed Jun. 26, 2020 to Office Action dated Mar. 24, 2020", (W/ English Translation of Claims), 13 pgs.

"Chinese Application Serial No. 201680034005.3, Response filed Aug. 27, 2020 to Office Action dated Apr. 27, 2020", with English claims, 9 pages.

"Australian Application Serial No. 2016263539, Response filed Sep. 9, 2020 to Subsequent Examiners Report dated Jul. 20, 2020", 18 pages.

"Australian Application Serial No. 2016263539, Subsequent Examiners Report dated Oct. 6, 2020", 3 pages.

"Australian Application Serial No. 2016263539, Response filed Oct. 8, 2020 to Subsequent Examiners Report dated Oct. 6, 2020", 24 pages.

* cited by examiner

… degree of freedom in translation with respect to the box. In this case, yet preferably, the translation is according to a horizontal axis.

From the perspective of implementing a degree of freedom for a positional adjustment guaranteeing, sufficient rigidity for each stable position of the support arm of the headrest, the support arm according to the invention includes at least one rail sliding in a slide of the chassis and cooperating with at least one integral guide shoe fastened to the chassis.

In practice, the guide shoe or shoes are preferably arranged at the exit of the slide or slides.

Yet according to a preferred embodiment, the support arm actually includes two lateral rails sliding in two slides facing each other and fastened to the chassis. This functional doubling plays a role in the stabilization of the support arm with respect to the chassis, since the stresses, which are applied to the arm during its displacements, are supported by two rails and thus reduced by half for each rail.

Finally, according to the invention, the free end of the support arm can be connected to the headrest through a radiotransparent part rigidly fastened to the free end of said support arm and including an interface for connection to head managing at least two degrees of freedom.

In general, the direct fastening system between the head of the patient and the robot is made with a reduced number of mechanical parts that are simple to be manufactured and to be assembled, which advantageously minimizes the risks of loss of mechanical stability/rigidity as much as the production costs. Another advantage of this relative simplicity can be seen in a mechanical robustness, which considerably reduces the needs for maintenance between uses.

The connection system between the head of the patient and the robot of the invention permits the complete robotic device to have, due to the retractability of the support arm, reasonable dimensions at the scale of an operating room, the size corresponding to the retracted state making it in addition easier to be stored.

Further peculiarities and advantages of the present invention will become evident from the detailed description of a non-restrictive exemplary embodiment of the invention shown in the attached figures.

Figure 1:
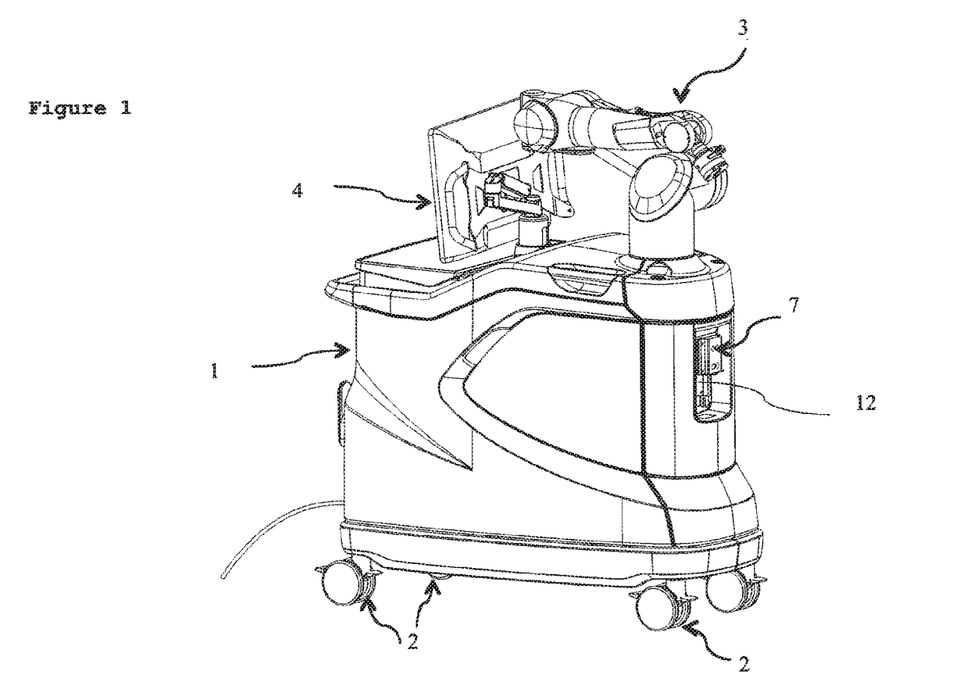
FIG. 1 is a perspective view of a neurosurgical assistive robot of the invention, the support arm of which is retracted.

With reference to FIG. 1, the neurosurgical assistive robot of the invention includes a movable box (1) on wheels (2) above which is mounted a robotic arm (3) the free end of which is provided with at least one tool. It also has an assistive screen (4) permitting the operator, in this case the surgeon, to visualize the operation in progress and more specifically the work of the tool provided on the robotic arm (3).

Figure 2:
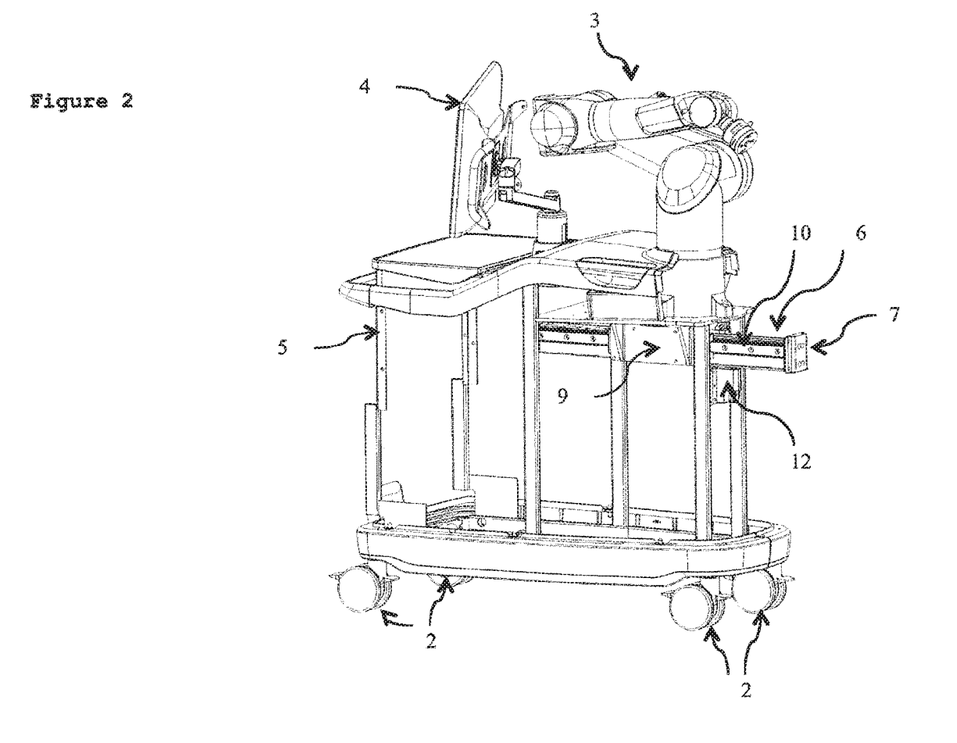
FIG. 2 shows said robot, the chassis being apparent, with the support arm partially extended.

The movable box (1) covers a chassis (5) visible in FIG. 2, provided with a rigid support arm (6) the function of which will be explained more in detail hereinafter. Said support arm (6) is movable relative to the chassis (5) between a position retracted in the volume of the box (1), or of the chassis (5), and a plurality of extended positions. It includes an end provided with a plate for fastening (7) to equipment, namely for maintaining the head of the patient.

In the pre-operative phase, an operator adapts the position of the neurosurgical assistive robot first roughly by moving the robot on its rollers (2), then more accurately by extending the support arm (6) depending on the positioning of the patient, thus with respect to the location of the operating table (18). Once the optimum position of the support arm (6) has been established, the invention provides for locking means (12) permitting to maintain said arm (6) rigidly in nearly any position. Thus, the head of the patient is maintained in a rigid and especially reliable way during the operation. Maintaining this rigidity and the precision of the stable positioning of the box (1)/chassis (5) carrying the robotic arm (3) relative to the patient is obviously quite capital for applications to brain surgery.

FIG. 1 shows the neurosurgical assistive robot with the support arm (6) in the retracted position inside the box (1). Advantageously, in this configuration, the movable box (1) is easy to be manipulated and transported in a congested environment such as an operating room.

Figure 3:
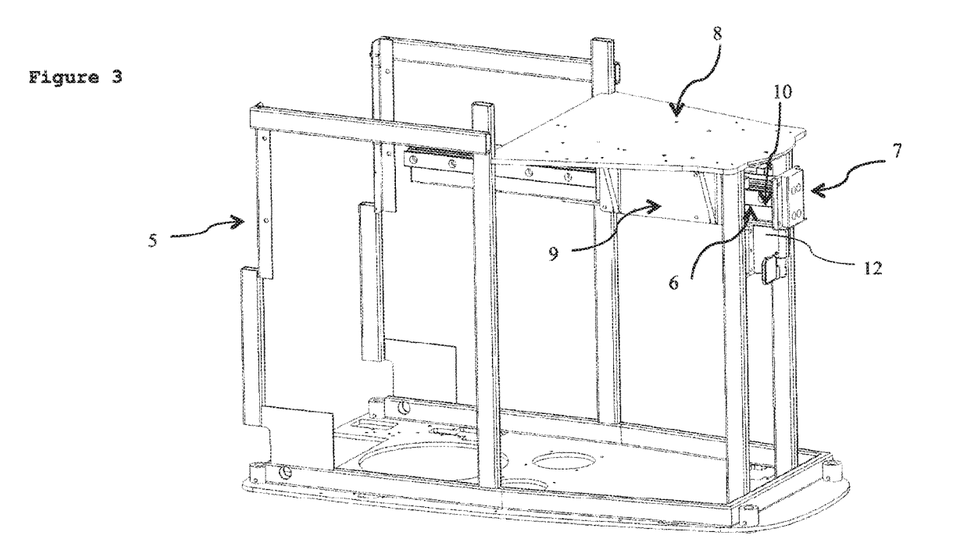
FIG. 3 shows the chassis of this robot, with the support arm fully retracted.
Figure 4:
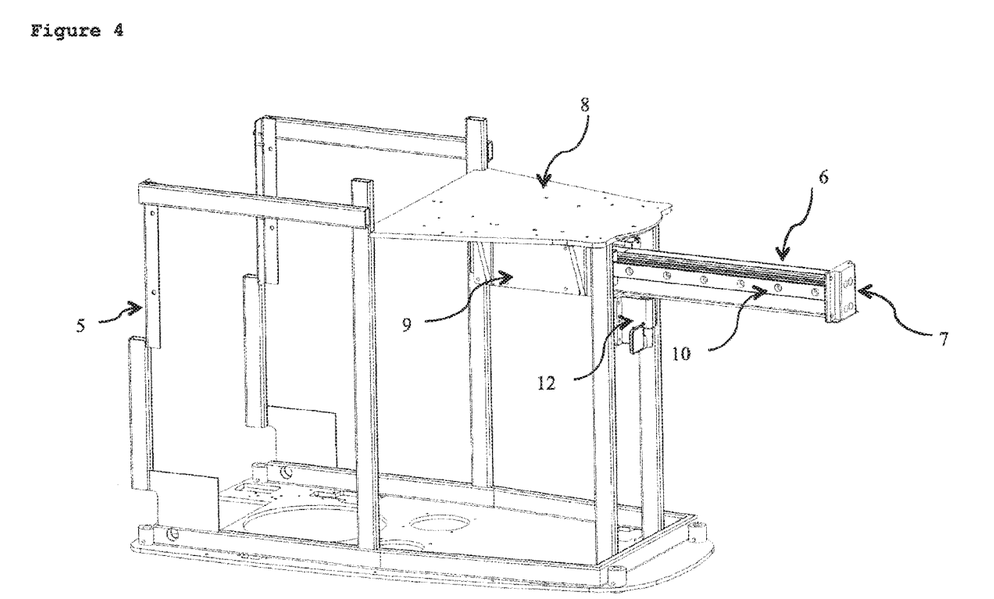
FIG. 4 is a representation of said chassis with the support arm fully extended.

FIG. 2 shows more particularly how the support arm (6) and the second robotic arm (3) are fastened to the neurosurgical assistive robot, in a way that guarantees the stability necessary for a surgical use related to the treatment of the brain. To this end, the chassis (5) comprises a rigid reference structure including namely a plate (8), more particularly visible in FIGS. 3 and 4, under which means for managing (9) the mobility of the support arm (6) (in this case, in translation) are fastened and on which the second robotic arm (3) is fastened.

Figure 5:
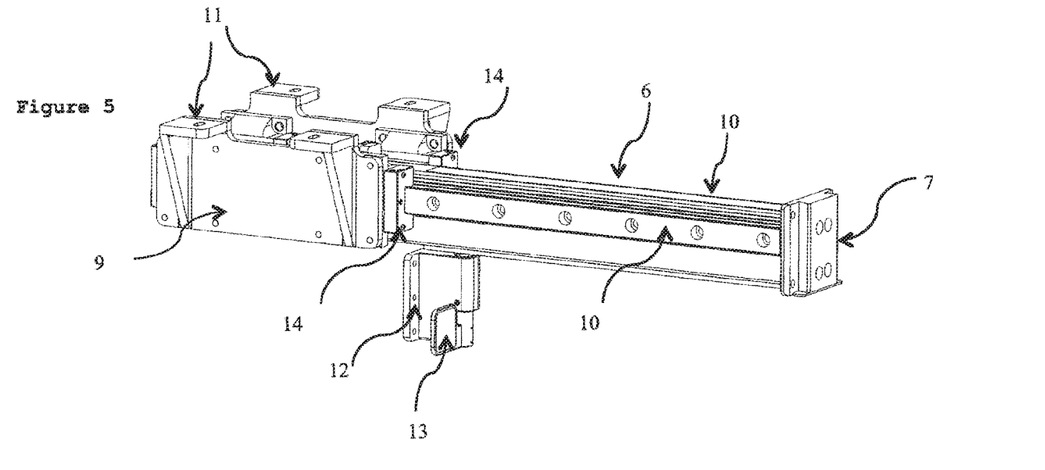
FIG. 5 shows the arrangement of the support arm and the slide in which it slides.

In practice, the support arm (6) is movable according to a single degree of freedom in translation with respect to the chassis (5). More particularly, the translation of the support arm (6) occurs along a horizontal axis. To this end, the chassis (5) comprises a guide block (9) shown in FIG. 5, provided with two slides facing each other, in which two lateral rails (10) slide. The latter are mounted on both sides of the vertical sides of the support arm (6) so as to correspond to the locations of the slides in the block (9). This arrangement permits to obtain a closely guided and hence very stable horizontal translation of said support arm (6) between two extreme, retracted and extended, positions, which are respectively visible in FIGS. 3 and 4.

The guide block (9) is fastened under the plate (8) made integral with the chassis (5), for example by bolting at the level of angle brackets (11). It comprises two guide shoes (14) arranged at the exit of the block (9), which facilitate the gliding during the sliding of the support arm (6). The guide shoes (14) cooperate in fact with the rails (10) mounted on the support arm (6) and optimize the precision of the translation of the support arm (6).

Advantageously, the guide shoes (14) also contribute to a reliable maintaining of the position of the support arm (6) in the extended position, even when considerable stresses are exerted onto the head of the patient, which stresses are passed onto the arm (6), as will be seen hereinafter.

In order to ensure even more the stability and rigidity of the connection, in addition to the guiding itself, the shape of the accommodation inside the block (9) corresponds to the outer shape of the arm (6), rails (10) included, which also improves the positioning of one in the other at any time during the displacement and for each extended position.

As mentioned above, the support arm (6) includes marking means (not shown), which are for example formed by graduations for marking the position of said support arm (6). This feature permits the operator, namely in the pre-operative phase, to pre-position with sufficient accuracy the neurosurgical assistive robot relative to the head of the patient.

Figure 6:
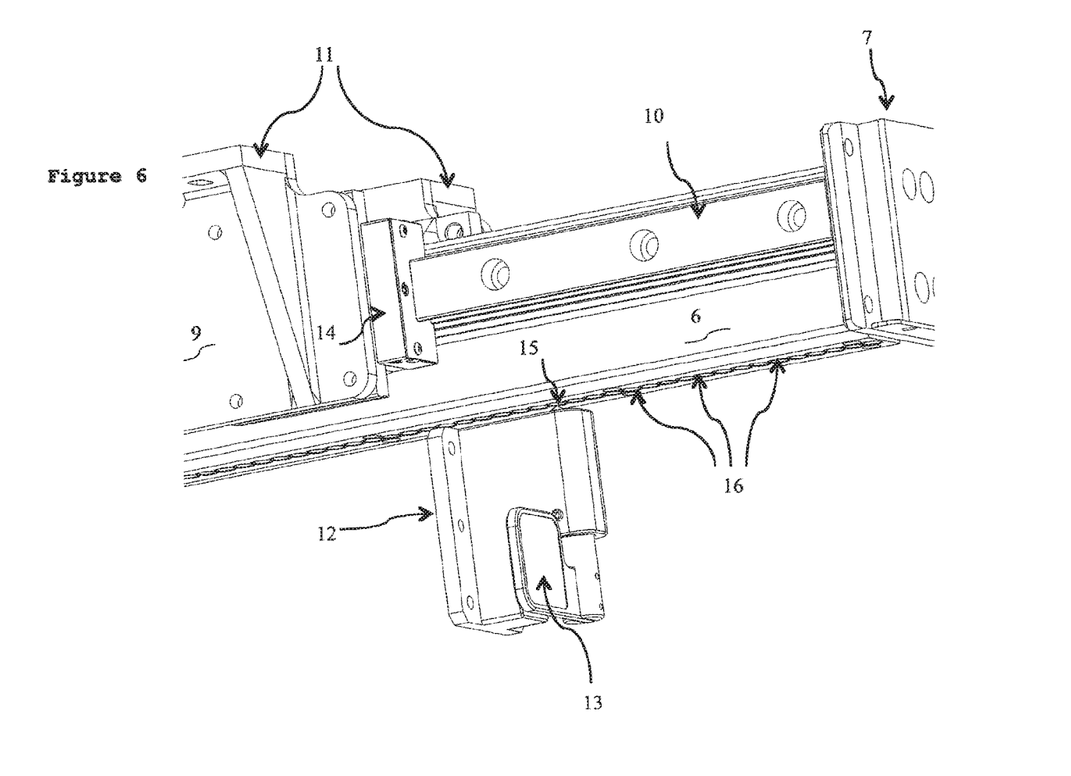
FIG. 6 shows, in a partial perspective view, the locking means provided for cooperating with the support arm, in the non-activated position.
Figure 7:
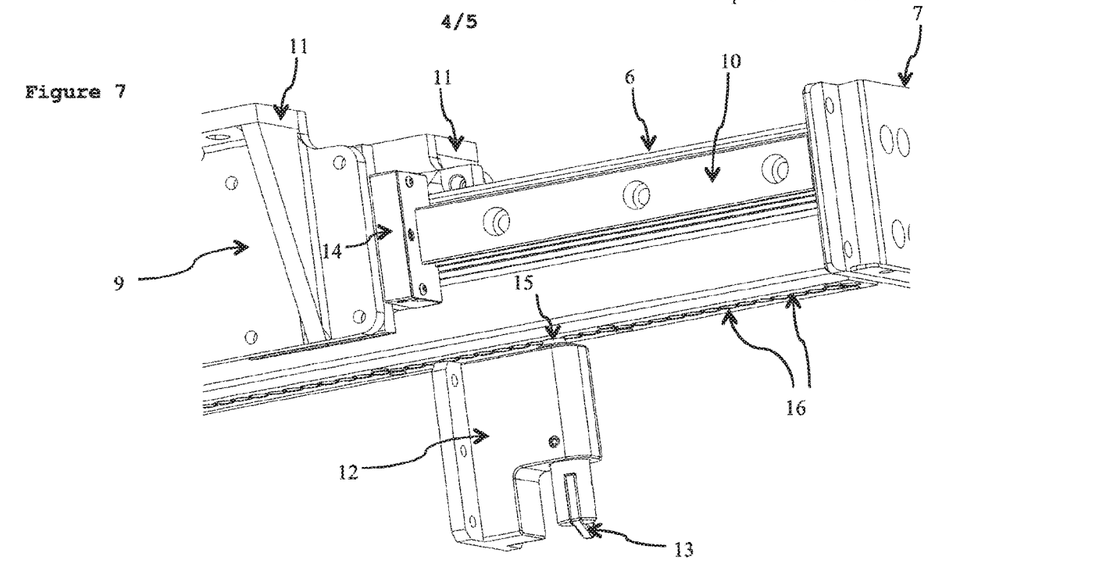
FIG. 7 shows said locking means in the activated position, rigidly blocking the support arm.

FIGS. 6 and 7 more particularly show the operation of the locking means (12) fastened to the chassis (5), said means (12) being placed at the exit of the slide (9) so as to permit an easy access to the control lever (13).

These locking means (12) include at least one indexing finger (15), the conical end of which, designed to be centered in holes (16) distributed at regular intervals in the lower face of the support arm (6), is shown in FIG. 6. This index finger (15) is biased by spring means towards these holes or recesses (16) made in the support arm (6). The spring means may, for example, be formed by a conventional compression spring.

More specifically, the conical free end of the finger (15), when it cooperates with the holes (16) arranged in the direction of displacement, permits the support arm (6) to adopt a large number of discrete stable positions with a dimensional accuracy that depends on the diameter of the holes. In the application of the invention, the finger (15) fits with minimal clearance in the holes (16) so as to prevent any uncontrolled, even small, displacement of the support arm (6).

The locking means (12) are activated/deactivated by a control lever (13), which is movable between at least two positions, an activation position, which is shown in FIG. 7, and a deactivation position, shown, for example, in FIGS. 5 and 6, respectively. The use of a movable control lever (13) such as that of the invention permits a fast and effective blocking of the translation of the support arm (6). The conical end of the finger (15), when it is centered in a hole (16), slightly modifies the dimensional setting initially chosen manually by the user in its presetting phase.

As shown in FIG. 6, when the control lever (13) is in the deactivated position, the indexing finger (15) is retracted in its accommodation recess against the spring means, and the operator can then freely adjust the position of the support arm (6) by translation.

Once the optimum position has been established, the operator moves the movable control lever (13) to the activated position, releasing the spring means, which bias and maintain the conical end of the index finger (15) in abutment in the hole (16) facing it, or in any case in the nearest hole (16) permitting a centering, the position and the to extension of the arm (6) then being locked.

Such locking means (12) permit a fast, reliable and robust immobilization of the support arm (6) in any position by rigid locking of the finger (15) in a hole (16) with a corresponding diameter. The position of the head of the patient can then be reliably maintained, i.e. with a sufficient degree of immobility of the structure, which supports it, even when considerable stresses are exerted onto the head of the patient.

Figure 8:
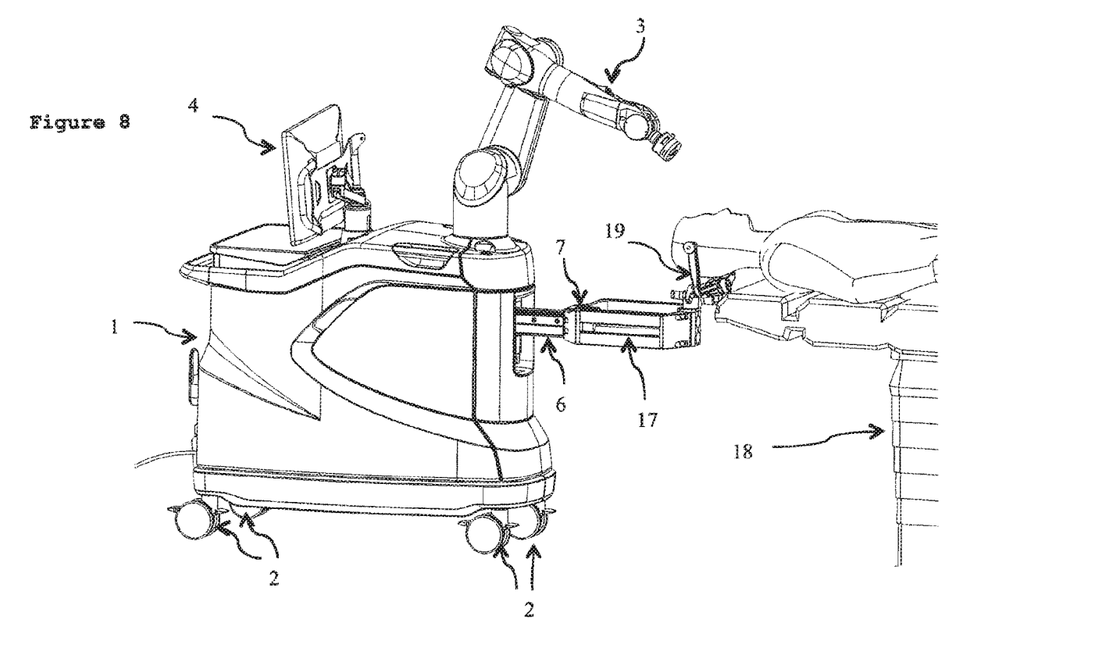
FIG. 8 shows the operation of the neurosurgical assistive robot of the invention for operating on the cranial cavity of a patient lying on an operating table.
Figure 9:
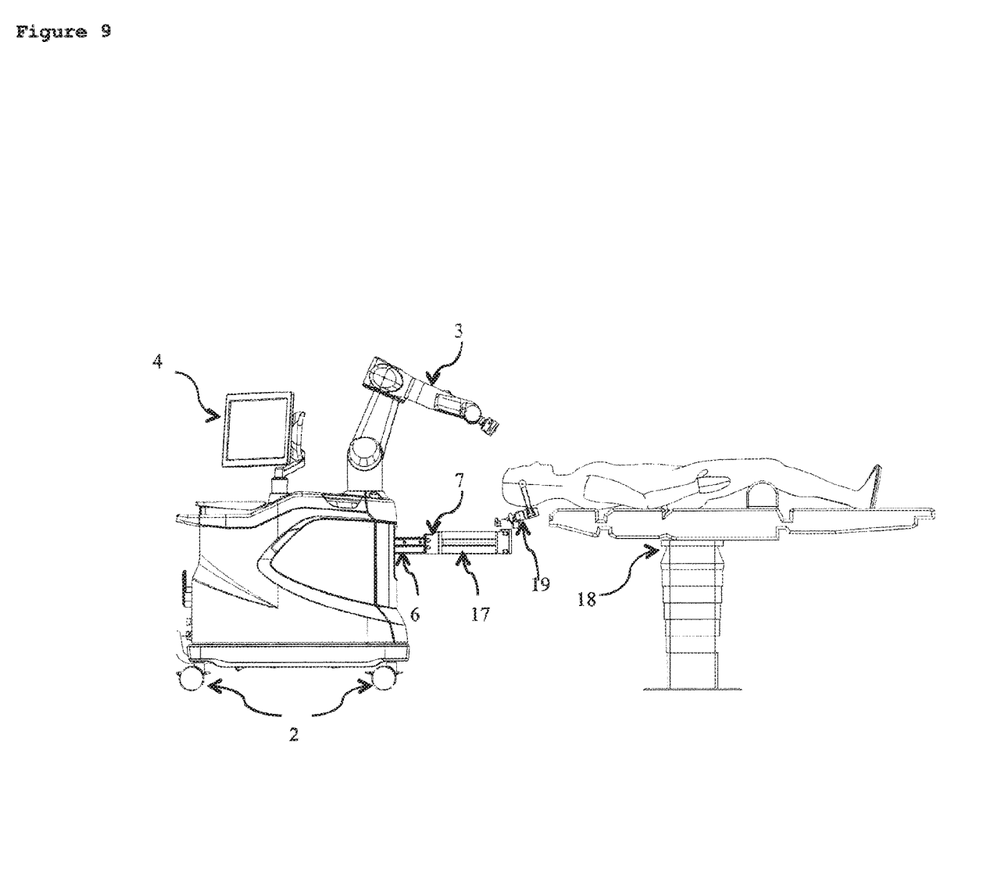
FIG. 9 shows the interaction between the robot and the patient, in a side view.

A possible mode of locking the head of the patient is indeed shown in FIGS. 8 and 9; the free end of the support arm (6) is in this case connected to a standard system (19) for locking the head of the patient lying on the operating table (18). In the configuration being shown, this locking is carried out via a radiotransparent part (17) attached to the plate (7), which adopts the form of a rigid frame. The radiotransparency of said part (17) permits, in the intra-operative phase, to make and obtain snapshots using imagers using X-rays by eliminating all radio-nuisances in the environment close to the head of the patient.

The radiotransparent frame (17) must absolutely be rigidly fastened to the free end of the support arm (6), since with it is made integral the standard system (19) for locking the head of the patient, through a connection interface managing at least two degrees of freedom. The relative mobility, when it is necessary, is thus taken over at this point in the mechanical chain.

The degrees of freedom of the interface part, for example attached to a standard headrest (19) as shown in FIGS. 8 and 9, permit to adapt even more accurately the positioning of the neurosurgical assistive robot with respect to the head of the patient during the operation. The mechanical management of the degrees of freedom is planned as close as possible to the head of the patient. Thus, when considerable stresses are exerted onto the head of the patient, which happens during operations involving preliminary work phases on the bony parts of the cranial cavity; the couple or the stresses exerted onto each connection managing a degree of freedom is or are reduced as much as possible.

In the example shown, the connection interface between the radiotransparent frame (17) and the standard headrest (19) has five degrees of freedom.

There are alternatives to the use of a standard headrest (19) for maintaining the head of the patient, which are perfectly usable within the scope of the present invention, for example devices based on a stereotactic frame with two degrees of freedom.

This possibility is not shown: in general, the configuration described by means of the figures is not exhaustive of the invention, which encompasses the variants of shape and of structure, namely, but not exclusively, as regards the dimensional adjustment of the robot of the invention in the extended position.

The invention claimed is:

1. A robotic apparatus for neurosurgical procedures, the robotic apparatus comprising:
    a robotic arm with a plurality of joints and an end effector adapted to hold at least one surgical tool;
    a chassis supporting the robotic arm and at least partially covered by a movable box;
    a rigid support arm movably coupled within the chassis and extendable from a first retracted position within the chassis to a plurality of extended positions where at least a portion of the rigid support arm extends outside the movable box, wherein a free end of the rigid support arm receives a radiotransparent extension to rigidly couple the free end of the rigid support arm to a headrest; and
    a locking mechanism integrated into the rigid support arm for locking the rigid support arm in any one of the plurality of extended positions.

2. The robotic apparatus of claim 1, wherein the rigid support arm further comprises an end plate affixed to an outbound end of the rigid support arm and adapted to receive equipment to immobilize a portion of anatomy of a patient.

3. The robotic apparatus of claim 2, wherein the end plate is adapted to receive a head restraint mechanism to retain a head of the patient.

4. The robotic apparatus of claim 1, further comprising an interface plate coupled to the chassis directly superior to a portion of the chassis securing the rigid support arm, the interface plate operating as a base for the robotic arm.

5. The robotic apparatus of claim 1, wherein the locking mechanism includes an indexing finger biased by a spring towards a plurality of recesses along a length of the rigid support arm.

6. The robotic apparatus of claim 5, wherein the indexing finger includes a conical free end that cooperates with the plurality of recesses to lock the rigid support arm in one of the plurality of extended positions.

7. The robotic apparatus of claim 1, wherein the locking mechanism is actuated by a control lever movable between at least two positions corresponding to an activation state and a deactivation state of the locking mechanism.

8. The robotic apparatus of claim 1, wherein the rigid support arm is movable in a single degree of freedom translating relative to the chassis.

9. The robotic apparatus of claim 1, wherein the rigid support arm comprises a pair of opposing sliding rails cooperating with a pair of guide shoes integrated into the chassis.

10. The robotic apparatus of claim 9, wherein the guide shoes are supported within a guide block secured to the chassis, the guide block containing the rigid support arm in the retracted position and supporting portions of the rigid support arm in the plurality of extended positions.

11. The robotic apparatus of claim 10, wherein the guide shoes are positioned at an exit of the guide block, wherein rigid support arm extends from the exit of the guide block.

12. A rigid support apparatus for movably coupling a robotic platform to an anatomical member, the rigid support apparatus comprising:
a rigid support arm extendable from a first position retracted within a chassis of the robotic platform to a second position where a free end of the rigid support arm extends external the chassis;
a guide block coupling the rigid support arm to the chassis and structured to support extension of the rigid support arm between the first position and second position; and
a locking mechanism to lock the rigid support arm in the second position, the locking mechanism including an indexing finger biased by a spring towards a plurality of holes along a length of an inferior surface of the rigid support arm.

13. The rigid support apparatus of claim 12, wherein the guide block includes a pair of slides mounted on opposing vertical sidewalls to receive a pair of lateral rails of the rigid support arm, the pair of lateral rails slidable within the slide to extend the free end into the second position.

14. The rigid support apparatus of claim 13, wherein the guide block includes a pair of guide shoes positioned at an exit end of the guide block to guide the pair of lateral rails of the rigid support arm.

15. The rigid support apparatus of claim 12, wherein the indexing finger includes a conical free end that cooperates with the plurality of holes to lock the rigid support arm in the second position.

16. The rigid support apparatus of claim 12, wherein the locking mechanism is actuated by a control lever movable between a first position corresponding to an activation state and a second position corresponding to a deactivation state.

17. The rigid support apparatus of claim 12, wherein the free end of the rigid support arm receives a radiotransparent extension to rigidly couple the free end of the rigid support arm to a headrest.

18. A robotic system comprising:
a robotic arm with a plurality of joints and an end effector adapted to hold at least one surgical tool relative to a portion of a patient's anatomy;
a chassis supporting the robotic arm and a guide block;
a rigid support arm movably coupled within the guide block and extendable from a first retracted position within the guide block to a plurality of extended positions where at least a free end of the rigid support arm extends outside a movable box, wherein the rigid support arm includes an end plate affixed to an outbound end of the rigid support arm and the end plate is adapted to receive a head restraint mechanism to immobilize a head of the patient;
an anatomical restraint mechanism adapted to restrain the portion of the patient's anatomy, the anatomical restraint mechanism coupled to the free end of the rigid support arm; and
a locking mechanism integrated into the chassis for locking the rigid support arm in any one of the plurality of extended positions.

19. A robotic apparatus for neurosurgical procedures, the robotic apparatus comprising:
a robotic arm with a plurality of joints and an end effector adapted to hold at least one surgical tool;
a chassis supporting the robotic arm and at least partially covered by a movable box;
a rigid support arm movably coupled within the chassis and extendable from a first retracted position within the chassis to a plurality of extended positions where at least a portion of the rigid support arm extends outside the movable box, wherein the rigid support arm includes an end plate affixed to an outbound end of the rigid support arm and the end plate is adapted to receive a head restraint mechanism to immobilize a head of the patient; and
a locking mechanism integrated into the rigid support arm for locking the rigid support arm in any one of the plurality of extended positions.

20. A robotic apparatus for neurosurgical procedures, the robotic apparatus comprising:
a robotic arm with a plurality of joints and an end effector adapted to hold at least one surgical tool;
a chassis supporting the robotic arm and at least partially covered by a movable box;
a rigid support arm movably coupled within the chassis and extendable from a first retracted position within the chassis to a plurality of extended positions where at least a portion of the rigid support arm extends outside the movable box; and
a locking mechanism integrated into the rigid support arm for locking the rigid support arm in any one of the plurality of extended positions, the locking mechanism including an indexing finger biased by a spring towards a plurality of recesses along a length of the rigid support arm.

21. A rigid support apparatus for movably coupling a robotic platform to an anatomical member, the rigid support apparatus comprising:
a rigid support arm extendable from a first position retracted within a chassis of the robotic platform to a second position where a free end of the rigid support arm extends external to the chassis, wherein the free end of the rigid support arm is adapted to receive a radiotransparent extension to rigidly couple the free end of the rigid support arm to a headrest;

a guide block coupling the rigid support arm to the chassis and structured to support extension of the rigid support arm between the first position and second position; and a locking mechanism to lock the rigid support arm in the second position.

\* \* \* \* \*

UNITED STATES PATENT AND TRADEMARK OFFICE
CERTIFICATE OF CORRECTION

PATENT NO. : 10,881,483 B2  
APPLICATION NO. : 15/576170  
DATED : January 5, 2021  
INVENTOR(S) : Nahum et al.

Page 1 of 1

It is certified that error appears in the above-identified patent and that said Letters Patent is hereby corrected as shown below:

On the Title Page

In item (57), in "Abstract", in Column 2, Line 5, delete "Accore" and insert --According to the-- therefor In item (57), in "Abstract", in Column 2, Line 9, delete "iled" and insert --position-- therefor In the Claims In Column 7, Line 38, in Claim 12, after "external", insert --to--

Signed and Sealed this  
Sixteenth Day of March, 2021

Drew Hirshfeld  
*Performing the Functions and Duties of the*  
*Under Secretary of Commerce for Intellectual Property and*  
*Director of the United States Patent and Trademark Office*